(12) United States Patent
Mitragotri

(10) Patent No.: US 6,589,173 B1
(45) Date of Patent: Jul. 8, 2003

(54) ULTRASOUND SYSTEM FOR DISEASE DETECTION AND PATIENT TREATMENT

(75) Inventor: Samir Mitragotri, Goleta, GA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/907,425

(22) Filed: Jul. 16, 2001

Related U.S. Application Data
(60) Provisional application No. 60/218,626, filed on Jul. 17, 2000.

(51) Int. Cl.[7] .................................................. A61B 8/00
(52) U.S. Cl. ....................................................... 600/437
(58) Field of Search ...................... 601/2; 600/437–472, 600/573, 567

(56) References Cited

U.S. PATENT DOCUMENTS

| | | | | |
|---|---|---|---|---|
| 5,398,690 A | * | 3/1995 | Batten et al. | 600/439 |
| 5,492,126 A | * | 2/1996 | Hennige et al. | 600/439 |
| 5,913,833 A | * | 6/1999 | Elstrom et al. | 600/573 |
| 6,007,497 A | * | 12/1999 | Huitema | 600/567 |

* cited by examiner

Primary Examiner—Marvin M. Lateef
Assistant Examiner—Ruby Jain
(74) Attorney, Agent, or Firm—Fulbright & Jaworski

(57) ABSTRACT

A device and method of detection and treatment of a solid cancer tumor, for example prostate cancer. In a diagnostic method, ultrasound is used to extract a cancer tumor marker from interstitial fluid into a coupling medium. In a method for treating a solid tumor, ultrasound is used to deliver one or more drugs from the coupling medium directly to the site of the tumor.

4 Claims, 3 Drawing Sheets

ULTRASOUND SYSTEM FOR DISEASE DETECTION AND PATIENT TREATMENT

CROSS-REFERENCE TO RELATED APPLICATION

This application claims the benefit of U.S. Provisional Patent Application Serial No. 60/218,626, filed Jul. 17, 2000.

FIELD OF THE INVENTION

The field of the invention is a system for detection and treatment of cancer.

BACKGROUND AND STATE OF THE ART

Currently, existing methods of diagnosing prostate cancer involve a series of steps and procedures; see Petrylak, infra; Potter,et al., infra; Naitoh, et al., infra; Hegarty et al., infra; Selley, et al., infra. The initial detection of signs that the patient may have prostate cancer is most commonly the result of some regular form of check-up carried out by a primary care physician, which includes a digital rectal examination. In this examination the physician inserts his finger into the rectum in order to be able to feel the size, shape, and texture of the prostate and other nearby organs. Although a highly experienced physician can make a relatively good diagnosis using digital rectal examinations ("DRE"), it is a "subjective" technique. The problem with using DREs to make decisions about what to do with particular patients is that two different experienced physicians may think that they feel quite different things when they carry out a DRE on the same patient. Neither of these physicians is necessarily right or wrong in what they think. They cannot see what they are feeling and they are doing their best to make wise decisions. Since the mid 1980's, prostate cancer diagnosis is performed by prostate specific antigen ("PSA") tests. The PSA test has revolutionized the detection of prostate cancer and monitoring of the effects of treatment. On its own, it is very probably responsible for the accurate diagnosis of prostate cancer in millions of men worldwide.

A PSA test measures the level of prostate specific antigen in the patient's blood. Using the most common type of PSA test currently available in the United States, the average, normal, healthy, 50-year-old male is generally believed to have a PSA of less than 4.0 nanograms per milliliter of blood (4.0 ng/ml). An elevated PSA level in blood may be associated with prostate cancer. Several modified versions of PSA tests can be performed to increase the reliability of the diagnosis. Although PSA tests have revolutionized prostate cancer diagnosis, it is not an absolute test of prostate cancer. Typically if both DRE and PSA tests are positive, a biopsy is taken. The biopsies of the prostate are carried out under ultrasound guidance. In this method, several samples of tissue are taken from the prostate using a method normally called sextant biopsy. In carrying out the actual biopsy, the biopsy needle is inserted into the prostate to take six or more samples of tissue from the prostate. The precise number of samples taken depends upon what the urologist is able to see using the ultrasound machine. This procedure is painful, uncomfortable, and may lead to bleeding complications.

Available methods of treatment for prostate cancer include hormone therapy, surgery, radiation therapy and cryotherapy; see Potter, et al., infra; Naitoh, et al., infra; Hegarty et al., infra; Selley, et al., infra. Hormone therapy is primarily used to treat patients who have prostate cancer that is not confined to the prostate. The intent of hormone therapy is first, to delay the progression of the cancer, and second, to increase the patient's survival while simultaneously maximizing his quality of life. Hormone therapy is limited by significant side effects.

The next available method of treatment for prostate cancer is surgical treatment, and is most common among younger, healthy patients, whose tumors are believed to be confined to the prostate (i.e., stages T1 or T2). There are two basic forms of surgery for removal of the prostate: radical retropubic prostatectomy and radical perineal prostatectomy. The only difference between these two techniques that is of importance to the patient, is that the surgeon uses different routes to reach the prostate. In radical retropubic prostatectomy the surgeon cuts down to the prostate through the lower abdomen. In a radical perineal prostatectomy, the surgeon cuts up to the prostate between the anus and the scrotum. All forms of surgery for removal of the prostate are associated with complications. These include lack of bladder control (urinary incontinence), urethra stricture (difficulty in urination), impotence, and the normal risks associated with anesthesia and major surgical procedures. There is general agreement that lower complication rates are usually found among those surgeons who carry out a significant number of prostatectomies on a regular basis. In other words, practice makes the surgeon more competent. However, even the best surgeons have patients with unexpected complications. Any form of prostatectomy is a major operation and has risks attached.

The third method for treatment of prostate cancer is radiation therapy. Radiation therapy is intended to treat the prostate cancer that is confined to the prostate and/or the surrounding tissues (i.e., clinical stages T1, T2, and T3). Radiation therapy is delivered using an external beam of x-rays carefully directed to the areas of the pelvis that include the prostate. Other forms of radiation therapy are "interstitial brachytherapy" (commonly known as seed implantation), in which the radiation oncologist and a surgeon implant radioactive pellets or "seeds" into the prostate, and those pellets radiate the prostate and the surrounding tissue over time. It is not uncommon for brachytherapy and external beam radiation therapy to be used in combination in appropriate patients. Like surgery, all forms of radiation therapy are associated with complications, including acute cystitis, proctitis, and enteritis. In addition, most series of radiotherapy patients have been associated with some subsequent urinary and sexual dysfunction.

Finally, cryotherapy is a means of treatment for prostate cancer. Cryotherapy is an old technique that has been reborn as a result of advances in technical capability. Rather than removing the prostate (as in conventional surgery) or using radiation therapy with different forms of x-rays, cryotherapy is a method of freezing the prostate and other appropriate nearby tissues to extremely low temperatures with liquid nitrogen. This technique is designed to kill all the prostate cancer tissue without having to take the risks involved in carrying out invasive surgery. The known side effects of cryotherapy can include impotence (in about 80% of patients), scarring of the urethra and urinary dysfunction (which are relatively unusual), and irritation of the bladder, the urethra, the rectal wall, and the genitalia. This last group of side effects can include pain on urination, a burning sensation during urination, frequent and unexpected urination, blood in the urine (hematuria), and swelling of the penis or the scrotum.

Thus, existing methods of diagnostics and treatment for prostate cancer suffer from several limitations. Specifically, the existing methods of diagnostics are invasive and inconvenient. The blood test for PSA is invasive and requires a blood sample. In addition, this method does not acquire a sample directly from the prostate. The existing methods of treatment also suffer from several limitations. Specifically, surgery and hormone therapy result in severe side effects. In addition, chemotherapy is limited by severe side effects of cytotoxic agents.

SUMMARY OF THE INVENTION

The present invention offers a device and method for performing a diagnostic test and/or treating disease, illustrated herein by cancer, that is an advantageous alternative to the existing methods of diagnostics and treatment. The device comprises is an ultrasound transducer and a reservoir connected to the transducer. The reservoir is in the form of a cartridge that is shaped to be placeable against the tissue in the region of the disease to be diagnosed or treated, e.g., at the site of a cancerous tumor such as prostate gland tissue, and contains a coupling medium to transmit unltrasound to the tissue whereby to produce cavitation for permeabilizing the tissue. The coupling medium can contain a cavitation enhancer. The method is illustrated with respect to the diagnosis and treatment of prostate cancer but is applicable to other forms of tumors, or other diseases that are accessible to a probe, such as pancreatic tumors, skin tumors, colon tumors, and cervical tumors.

In the case of diagnostics, the present invention uses ultrasound to extract a marker, such as a cancer tumor marker, into the coupling medium and provides advantages over existing methods: i) it is non-invasive with tumors in accessible locations, such the prostate gland, colon, or cervix; ii) it measures a marker associated with interstitial fluid associated with the tumor, e.g., PSA concentration in the interstitial fluid of the prostate, as opposed to systemic levels, which provides in increased diagnostic sensitivity; and iii) it is convenient to use.

In the case of treatment, the present invention uses ultrasound to deliver one or more drugs from the coupling medium directly to the site of the disease and provides advantages over existing methods: i) it is non-invasive with disease sites in accessible locations, as above; ii) it delivers drugs locally to the site, thus limiting side effects; and iii) it is painless.

In particular, the present invention consists of the following major components: i) an ultrasound transducer probe placed in contact with the body; ii) a power source to activate the ultrasound probe; iii) a reservoir attached to the transducer to collect extracted markers or to hold the drugs to be delivered; and iv), for diagnostic procedures, a detection method to measure the concentration of extracted markers.

DETAILED DESCRIPTION OF THE INVENTION

Figure 1:
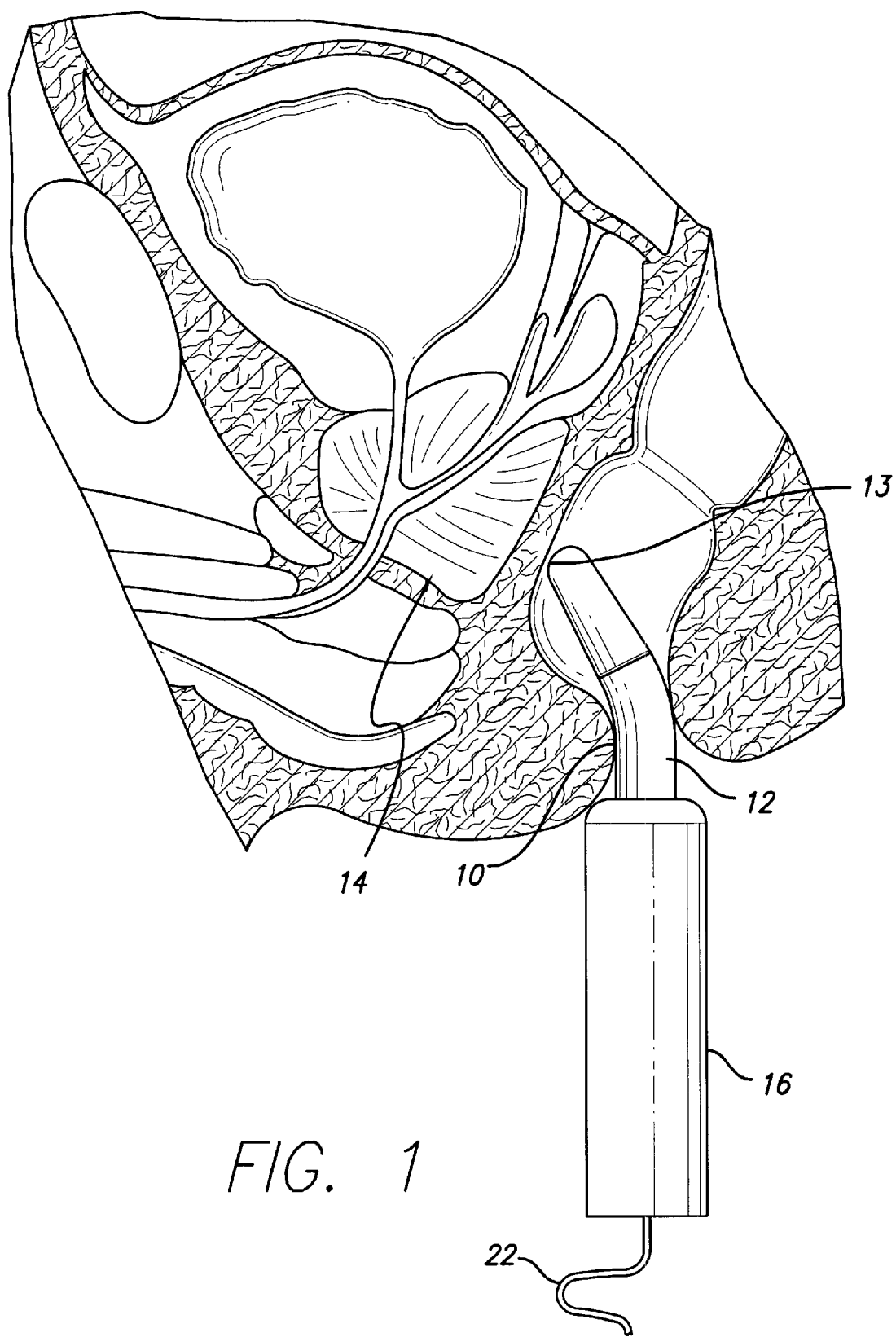
FIG. 1 is a cross-sectional drawing of the rectal region of the male body with a schematic representation of an ultrasonic probe of this invention inserted through the rectum and placed against the prostate.
Figure 2:
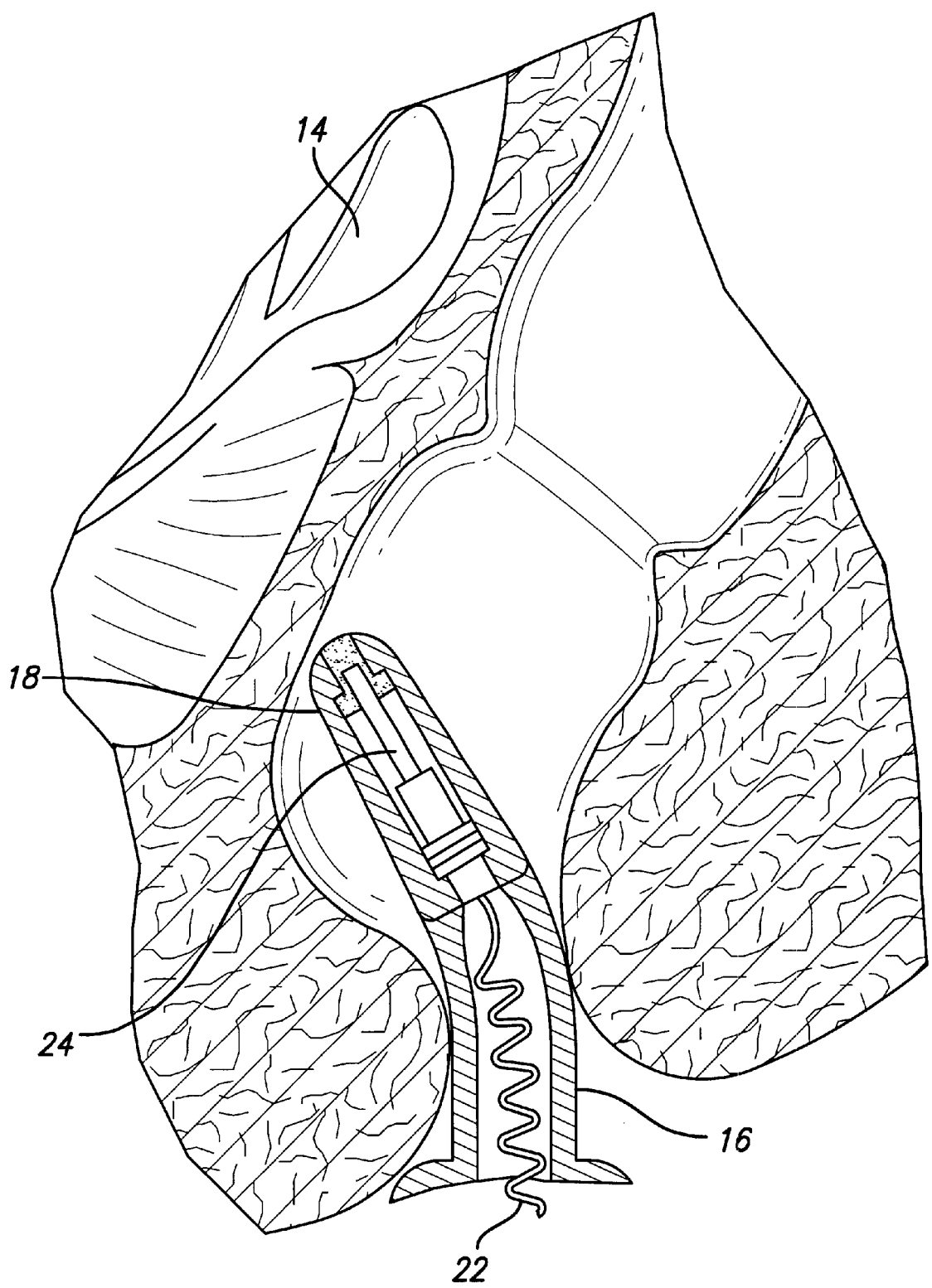
FIG. 2 is a close view of the region in the dashed circle of FIG. 1.
Figure 4:
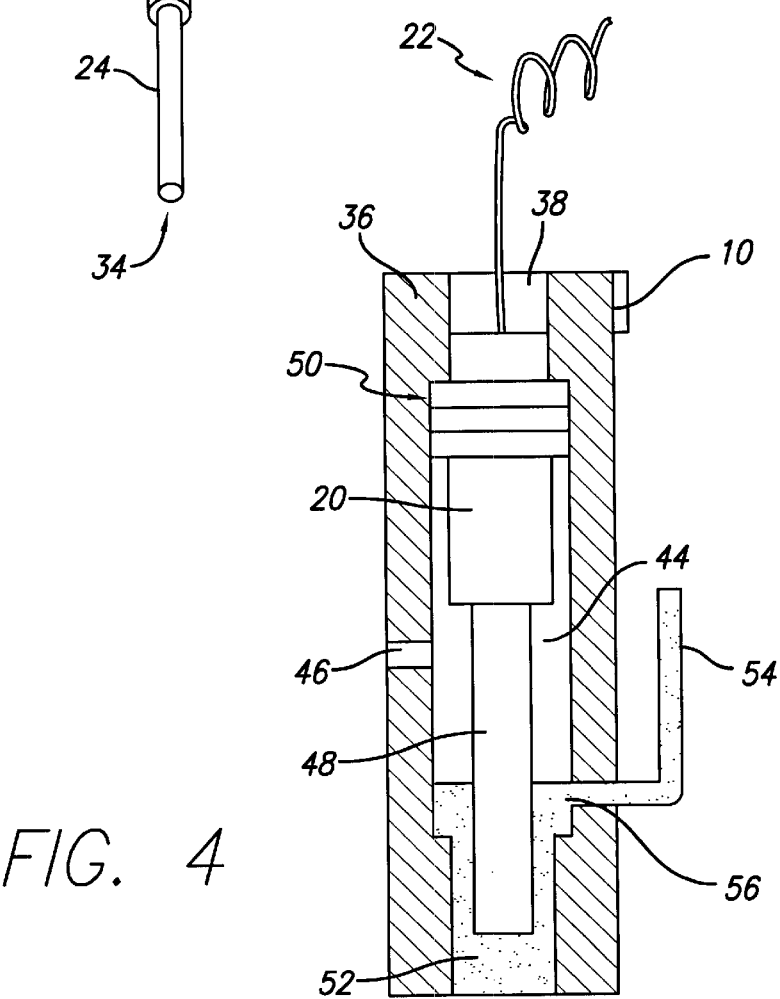
FIG. 4 is a detailed structure of ultrasound transducer cartridge of this invention.

Referring to FIGS. 1, 2 and 4, an ultrasound transducer cartridge 10 is inserted through the patient's anus 12 to be placed against tissue 13 of a patient's prostate gland 14. The cartridge 10 is shown with schematic depictions of only certain components, and will be described with more detail hereinafter with respect to FIG. 4. The cartridge 10 contains a handle 16 supporting a reservoir chamber 18 adjacent which is located an ultrasound transducer 20 receiving power from a power and signal cord 22. The reservoir contains a coupling medium, which is an important component of the system. It serves a number of purposes: i) transmission of ultrasound from the transducer to the tissue; ii) production of cavitation for tissue permeabilization; iii) collection of cancer markers extracted from the tissue; and iv) storage of drugs to be delivered into the tissue. In order to couple ultrasound effectively, it is important that the acoustic impedance of the medium matches with that of the tissue. This can be easily achieved by using water as a primary component of the coupling medium. A gel may be used instead of water in the final product. Such a gel can comprise a water based hydrogel for collection of interstitial fluid or a hydrophobic gel for incorporation of the drug.

The second purpose of the coupling medium is to produce cavitation. The coupling medium may have cavitation enhancers to aid in tissue permeabilization. Cavitation enhancers include polymer microspheres, e.g., having diameters in the range of 50 to 100 microns. The concentration of the particles is in the range of 0.001% to 0.1%, preferably about 0.01%. These particles are relatively large and are unlikely to penetrate into the tissue. Instead, they remain in the coupling medium and enhance cavitation. Alternatively, or in addition, the coupling medium may contain chemical enhancers such as sodium alkyl sulfates, and surfactants such as SPAN, TWEEN, CTAB, or their mixtures. Typical concentrations of these enhancers in the coupling medium is up to about 1%. These enhancers are known to enhance transport in tissues in the presence of ultrasound; see Mitragotri, (1999), infra. Unlike microparticles, chemical enhancers penetrate into the tissue and enhance transport therein.

Figure 3:
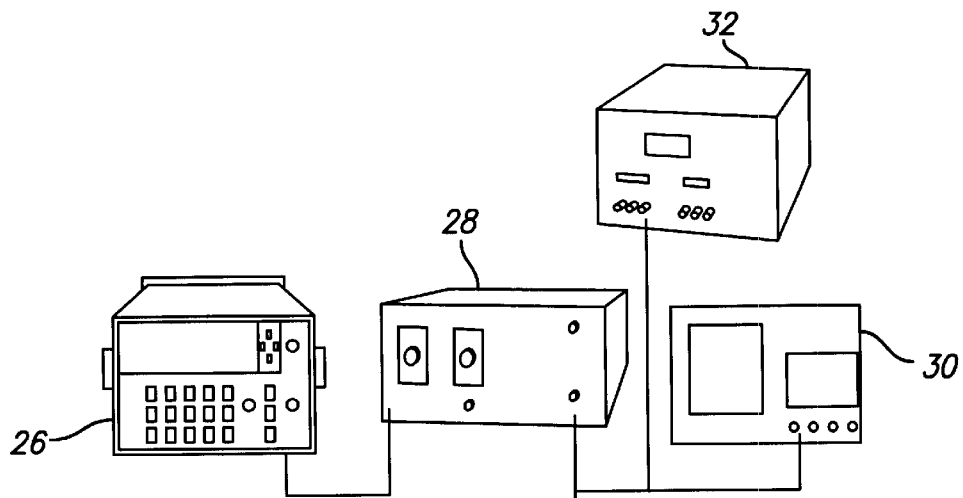
FIG. 3 is a schematic representation of the electronic components used in an ultrasound generation and application system of this invention.

Ultrasound is generated in the transducer 24 of the transducer cartridge 10 using components schematically represented in FIG. 3. The system consists of a signal generator 26, an amplifier 28, an oscilloscope 30, a wattmeter 32, and the transducer 24. The signal generator 24 generates a sinusoidal waveform at a desired frequency, e.g., in the range of 20 kHz–1000 kHz. This signal is amplified by the power amplifier 26 and then fed to the transducer 24 operating at the signal frequency of 20 kHz–1000 kHz. The transducer 24 converts the electrical energy into ultrasound, which is emitted from the distal end 34 of the transducer 24. The wattmeter 32 and the oscilloscope 30 monitor the performance of the system. The intensity of ultrasound is maintained between 0 and10 W/cm$^2$ using control mechanisms in the signal generator 26 and amplifier 28. All of the components shown in FIG. 3 are off-the-shelf items; their operation and interconnections are known.

A more detailed schematic depiction of the cartridge 10 is shown in FIG. 4. The cartridge 10 comprises a housing 36 formed with central bore 38 with opposing lands 40 and 42 defining a chamber 44 and having a vent hole 46 for air escapement from the chamber 44. The ultrasound transducer 20 is formed with an aluminum rod 48 extending from a piezoelectric ceramic 50 secured to one of the lands 42 and is powered by the power and signal cord 22. The chamber 44 and lower part of the bore 38 contains coupling medium 52 which is supplied by means of a port tube 54 connected to a port hole 56 through the cartridge housing 36 into the chamber 44. The chamber 44 and lower part of the bore 48 is shown only partly filled with coupling medium 52, but it is preferred to completely fill it, particularly when the cartridge 10 is used with the open side up. When the cartridge is used with the open side down, it need be filled sufficiently to transmit ultrasound via the coupling medium 52 to the tissue be diagnosed or treated. In either case, in use, the open face of the cartridge 10 is placed against the tissue, then coupling medium is added through the port tube 54.

The selection of ultrasound parameters is important and the effect of ultrasound on prostate permeability (or the permeability of other solid tumor tissue) depends on several ultrasound parameters including, frequency, intensity, and pulse length. Ultrasonic transport enhancement varies inversely with the ultrasound frequency due to an increase in cavitation activity at low ultrasound frequencies. Hence, a relatively low-frequency region (20 kHz–1000 kHz) is chosen for this application, and within this region, a frequency range of 20–100 kHz is preferred.

The sonophoretic enhancement also depends on the ultrasound intensity. This is expected since cavitational effects vary non-linearly with ultrasound intensity. The cavitation threshold at a frequency of 20 kHz in tap water is less than 1 W/cm2. This threshold increases with increasing frequency. Hence, a frequency range of 0–10 W/cm2 is chosen. The intensity is adjusted by the physician in situ.

The ultrasound pulse length can be applied either in a continuous mode or in a pulsed mode, e.g. at a pulse period in the range of a microsecond to a 300 hundred milliseconds. A pulsed mode of ultrasound application is used in practice because it can reduce the severity of adverse side effects of ultrasound, such as thermal effects. In addition, effects caused by acoustic streaming and standing waves are also significantly reduced by the pulsed application of ultrasound. A duty cycle in the range of 10% to 50% is preferable. The time for application for both diagnostic and treatment modalities is from a few seconds to a minute. Longer exposure to the ultrasound may be warranted as determined by experience in use.

Diagnostic System

After ultrasound is applied to the prostate, the transducer is taken out and the coupling medium is recovered. Concentration of one or more of the three markers, PSA, prostate specific membrane antigen ("PSMA"), and thymosin β15, are measured in the extracted fluid. PSA has been one of the most characterized prostate cancer markers that is secreted by normal epithelial cells of the prostate, and is more abundant in prostate carcinoma cells. Occasionally, however, late stage aggressive tumors stop producing PSA. In contrast to PSA, PSMA and thymosin β15 are not produced by normal prostate cells and are not normally found in low grade human prostate cancers; see Gleason; Naitoh, et al., infra; Hegarty, et al., infra; Selley, et al., infra. Consequently, their presence is an indicator of a higher grade, more aggressive tumor. This feature allows utilization of these markers as predictive assays that can help determine whether the patient has metastatic tumor. PSMA is a membrane antigen that is easily detected on the cell surface but is harder to detect in plasma. Thymosin β15 is a newer prostate cancer marker. It exists at two distinct locations: i) inside the cells where it remains bound to actin monomers and ii) outside the cells where it can be easily detected by competitive ELISA that can detect in nanogram quantities.

Unlike PSA, thymosin β15 and PMSA are not lost as tumor progresses to the metastatic stage. As mentioned earlier, the markers are extracted from the prostate into the coupling medium. Detection of the markers are performed using ELISA. The physician will make a diagnosis based on the measured concentrations of one or more of these markers.

Drug Delivery System

Drugs to be delivered are placed in the coupling medium and the ultrasound probe will then be placed against the prostate. Several drugs can be delivered via this route including estramustine phosphate, paclitaxel, and vinblastine. Several chemotherapeutic agents including estramustine phosphate, paclitaxel, and vinblastine have been studied for the treatment of prostate cancer. However, chemotherapy has not been at the forefront of prostate cancer treatment since many (indeed most) of these cytotoxic pharmaceuticals also have potentially severe side effects. Hence, if given systemically, they are likely to cause undesirable side effects. This problem is overcome by delivering these drugs locally to the prostate. Estramustine phosphate and paclitaxel (taxol) have a direct effect on certain specific structural components of cancer cells. Several studies have indicated the effectiveness of these drugs in treating refractory prostate cancer. Recent clinical trials have demonstrated the superiority of estramustine-vinblastine combination for the treatment of prostate cancer. In view of these data, the aforementioned drugs are chosen for the study. In addition to testing them individually, plans to assess the effect of their combinations on prostate cancer are ongoing. The required drug dose varies from patient to patient. Hence, it is important to control the drug dose using ultrasound parameters.

EXAMPLE

In one configuration, the physician loads a cartridge 10 into the handle 16 of the ultrasound probe and the probe is then inserted through the rectum such that the cartridge 10 is placed against the prostate, as shown in FIGS. 1 and 2. Ultrasound is activated for a predetermined time and the probe is then removed. The cartridge 10 is then removed from the probe and is placed into a device where the concentration of the aforementioned cancer markers in the cartridge is measured. A diagnosis of cancer is then made based on the test results. The same device may also be used for drug delivery. In that case, the physician will load a different cartridge 10 that contains one or more of the above drugs. The probe is placed against the prostate and is activated for a predetermined time. The device may be used by the physician only once (during the routine check-up) or multiple times (to deliver drugs or follow-up the treatment). Thus, this method will provide a non-invasive device for diagnosis and treatment of prostate cancer.

REFERENCES

The following references are each incorporated herein by reference.

Bao L, Loda M, Janmey P A, Anand-Apte B, Zetter B R. Thymosin β15: A novel regulator of tumor cell motility upregulated in metastatic prostate cancer. Nature Medicine. 1996; 2:1322–1328.

Hegarty, N. J., Fitzpatrick, J. M., Richie, J. P., Scardino, P. T., deVere, White, R. W., Schroder, F. H. and Coffey, D. S. Future prospects in prostate cancer. Prostate. 1999, 40, 261–8.

S. Mitragotri, D., Ray, J. Farrell, M. Tang, B., Yu, J. Kost, D. Blankschteing, R. Langer, "Synergistic effect of ultrasound and sodium lauryl sulfate on transdermal transport," J. Pharm. Sci, 89(7), 892–900 (2000)

Naitoh, J., Zeiner, R. L. and Dekernion, J. B. Diagnosis and treatment of prostate cancer. Am Fam Physician. 1998, 57,1531–9.

Petrylak, D. P. Chemotherapy for advanced hormone refractory prostate cancer. Urology. 1999, 54, 30–5.

Potter, S. R. and Partin, A. W. Prostate cancer: detection, staging, and treatment of localized disease. Semin Roentgenol. 1999, 34, 269–83.

Selley, S., Donovan, J., Faulkner, A., Coast, J. and Gillatt, D. Diagnosis, management and screening of early localized prostate cancer. Health Technol Assess. 1997, 1,1–96.

What is claimed is:

1. A diagnostic method comprising applying an ultrasound generating probe and a reservoir containing a coupling medium to tissue at a preselected site of a suspected cancerous tumor having associated therewith at least one cancer marker in or on a patient's body, applying ultrasound from said transducer to said preselected site and thereafter extracting a fluid, or its constituents, from said region into said reservoir, measuring the concentration of said at least one cancer marker in said fluid and making a diagnosis based on the measurement.

2. The method of claim 1 wherein said region is in the prostate, pancreas, colon, intetine, testicles, or skin.

3. The method of claim 1 wherein ultrasound is applied by direct contact of the tissue by an ultrasound generating probe.

4. A method for diagnosing the presence of a cancerous tumor in the prostate of a patient, comprising applying an ultrasound generating probe and a reservoir containing a coupling medium to the patient's prostate tissue at a preselected site of a suspected cancerous tumor having associated therewith at least one cancer marker selected from the group consisting of prostate specific antigen, prostate specific membrane antigen, and thymosin β15, applying ultrasound from said transducer to said preselected site and thereafter extracting a fluid, or its constituents, from said region into said reservoir, measuring the concentration of said at least one cancer marker said fluid and making a diagnosis based on the measurement.

* * * * *